(12) United States Patent
Gallagher et al.

(10) Patent No.: US 9,067,050 B2
(45) Date of Patent: Jun. 30, 2015

(54) ARTERIOVENOUS SHUNT HAVING A FLOW CONTROL MECHANISM

(75) Inventors: John Gallagher, Clonsilla (IE); Gerry McCaffrey, Tuam (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 537 days.

(21) Appl. No.: 13/435,371

(22) Filed: Mar. 30, 2012

(65) Prior Publication Data

US 2013/0261531 A1    Oct. 3, 2013

(51) Int. Cl.
| A61M 5/00 | (2006.01) |
| A61M 39/28 | (2006.01) |
| A61F 2/07 | (2013.01) |
| A61M 5/168 | (2006.01) |
| A61B 17/11 | (2006.01) |
| A61F 5/00 | (2006.01) |

(52) U.S. Cl.
CPC .............. *A61M 39/28* (2013.01); *A61F 2/07* (2013.01); *A61F 2002/072* (2013.01); *A61F 5/004* (2013.01); *A61M 5/16813* (2013.01); *A61B 17/11* (2013.01); *A61B 2017/1139* (2013.01); *A61B 2017/1107* (2013.01)

(58) Field of Classification Search
CPC ..... A61F 2/07; A61F 2002/072; A61F 5/004; A61F 5/0046; A61F 5/0053; A61F 5/0059; A61F 5/0066

USPC ...................... 623/1.12, 1.13, 1.15
See application file for complete search history.

(56) References Cited

U.S. PATENT DOCUMENTS

| 7,059,330 B1 * | 6/2006 | Makower et al. ............. 128/898 |
| 7,918,865 B2 * | 4/2011 | Liddicoat et al. ............. 606/139 |
| 2007/0299384 A1 | 12/2007 | Faul et al. |
| 2008/0281249 A1 | 11/2008 | Gertner |
| 2009/0062669 A1 | 3/2009 | Akingba |
| 2009/0270971 A1 * | 10/2009 | Xiao et al. ................... 623/1.14 |
| 2010/0030322 A1 | 2/2010 | Lee |
| 2010/0094401 A1 * | 4/2010 | Kolbel et al. ................ 623/1.13 |

OTHER PUBLICATIONS

Zaleski Gx, Funaki B, Gentile L, Garofalo Rs. Purse-String Sutures and Miniature Tourniquet to Achieve Immediate Hemostasis of Percutaneous Grafts and Fistulas: A Simple Trick with a Twist. *AJR* 2000; 175:1643-1645.

* cited by examiner

*Primary Examiner* — Leslie Deak
*Assistant Examiner* — Kai Weng (57) ABSTRACT

An arteriovenous shunt assembly including a shunt and a pull wire operated flow control mechanism. The shunt has a tubular body that defines a fluid passageway between a first end and a second end thereof The pull wire mechanism includes a portion disposed around the tubular shunt in at least one loop. The at least one loop may be selectively tightened or loosened remotely from the shunt to regulate the rate of blood flow through the tubular shunt.

15 Claims, 7 Drawing Sheets

ARTERIOVENOUS SHUNT HAVING A FLOW CONTROL MECHANISM

FIELD OF THE INVENTION

The invention relates to an arteriovenous (AV) shunt assembly having a flow control mechanism for regulating flow there through.

BACKGROUND OF THE INVENTION

In modern medicine there are numerous treatment situations in which it is desirable to create shunts or flow-through connections between blood vessels and/or other anatomical structures of the body. Such treatments include, for example, hemodialysis, hemofiltration, hemodiafiltration, plasmapheresis, and extracorporeal membrane oxygenation (ECMO). In many cases, open surgical techniques have been used to form anatomic connections or fistulas between adjacent vessels of body structures. More recently, percutaneous catheter-based techniques and devices have been developed for creating channels or passageways between adjacent vessels or anatomical structures.

In addition to the above-listed treatments, arteriovenous (AV) shunt devices have been proposed for treating chronic obstructive pulmonary disease (COPD) and drug-resistant hypertension. COPD, also called chronic obstructive airway disease, is a syndrome that may be caused by a number of different diseases, all of which damage the alveoli and bronchioles, leading to impaired lung function. These diseases include asthmatic bronchitis, chronic bronchitis (with normal airflow), chronic obstructive bronchitis, and emphysema. As the alveoli and bronchial tubes are destroyed, the remaining healthy lung tissue must work harder to provide the required amount of blood oxygenation. The need for more air leads to lung over-inflation. As the lung over-expands, it gradually enlarges, completely filling the chest cavity and causing a sense of shortness of breath. The lung eventually loses its elasticity and the combination of a larger, less elastic lung and damaged, nonfunctioning tissue leads to slower airflow into and out of the lung, resulting in the feeling in the patient of an obstructed airway.

One manner of treating COPD is oxygen therapy, which requires a patient to remain near a stationary oxygen source or carry a bulky portable oxygen source when away from home or a treatment facility. Understandably such oxygen therapy has many disadvantages. One surgical treatment that has been proposed for treating patients with COPD is lung reduction surgery. Such surgery, however, can be used on only a small percentage of the total patient population, requires long recovery times, and does not always provide a clear patient benefit.

Arteriovenous (AV) shunt devices for treating COPD provide a fistula between an artery and a vein that are anatomically parallel to each other. The approach is to create an arteriovenous fistula by implanting a shunt-like device between two major blood vessels in the leg, utilizing cardiovascular reserve to overcome respiratory insufficiency and improve oxygenation to the lungs. The shunt allows oxygen-rich blood from the artery to flow to the vein and thereby increases the oxygen content of the blood returning to the heart and lungs, which in turn is considered to benefit a patient suffering from COPD. The implantation of the shunt can increase cardiac output by about one liter per minute, without impacting heart rate or oxygen consumptions.

Such shunt devices have been suggested to be implanted via an open surgical procedure or via a minimally invasive intravascular surgical procedure, depending on the specific arterial and venous locations that are to be connected by the AV shunt. A need continues to exist in the art for an AV shunt that may be quickly and simply delivered and deployed via a minimally invasive intravascular procedure. In addition, after the AV shunt is implanted, the flow through the shunt may need to be adjusted in order to maximize the benefit or improvement to the patient's condition. Accordingly, embodiments hereof relate to an AV shunt assembly that is delivered in a minimally invasive procedure to create a fistula between adjacent vascular structures, whereby the flow through the shunt may be selectively adjusted in situ.

BRIEF SUMMARY OF THE INVENTION

Embodiments hereof relate to an arteriovenous shunt assembly that includes a tubular shunt, a flow control mechanism, and a subcutaneous control port. The flow control mechanism includes a pull wire having a distal portion disposed around the tubular shunt in at least one loop. The subcutaneous control port contains ends of the pull wire, and pulling on the wire causes the pull wire to selectively tighten around the tubular shunt and radially constrict the tubular shunt, thereby reducing the rate of blood flow through the fluid passageway of the tubular shunt.

Embodiments hereof also relate to a method for forming a fistular connection between first and second body vessels, the connection including means for adjusting the rate of blood flow therethrough. A shunt assembly is intravascularly delivered in its collapsed configuration to a tissue tract formed between the first second body vessels. The shunt assembly includes a tubular shunt that defines a fluid passageway between open first and second ends thereof and a flow control mechanism coupled to the shunt, wherein the flow control mechanism includes a continuous pull wire having a distal portion disposed around the tubular shunt in at least one loop. The tubular shunt is positioned through the tissue tract, and the tubular shunt is deployed to an expanded configuration. Shortening the pull wire tightens the at least one loop of the distal portion to radially constrict the tubular shunt and thereby reduce the rate of blood flow through the fluid passageway of the tubular shunt.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description with respect to components that have a mechanical memory to return to an expanded deployed configuration from a compressed or constricted delivery configuration. Non-exhaustive exemplary materials that may be used to form self-expanding components include stainless steel, a pseudo-elastic metal such as a nickel titanium alloy (nitinol), a polymer, or a so-called superalloy, which may have a base metal of nickel, cobalt, chromium, or other metal. Mechanical memory may be imparted to a wire or tubular structure by thermal treatment to achieve a spring temper in stainless steel, for example, or to set a shape memory in a susceptible metal alloy, such as nitinol, or a polymer such as any of the polymers disclosed in U.S. Pat. Appl. Pub. No. 2004/0111111 to Lin, which is incorporated by reference herein in its entirety.

The following detailed description is merely exemplary in nature and is not intended to limit the invention or the application and uses of the invention. Although the description of the invention is in the context of an AV shunt for the treatment of a patient suffering from COPD and related conditions, embodiments hereof may also be used as a shunt for treatment of other conditions and/or may be used to bridge any anatomical lumens or conduits where it is deemed useful. Furthermore, there is no intention to be bound by any expressed or implied theory presented in the preceding technical field, background, brief summary or the following detailed description.

Figure 1:
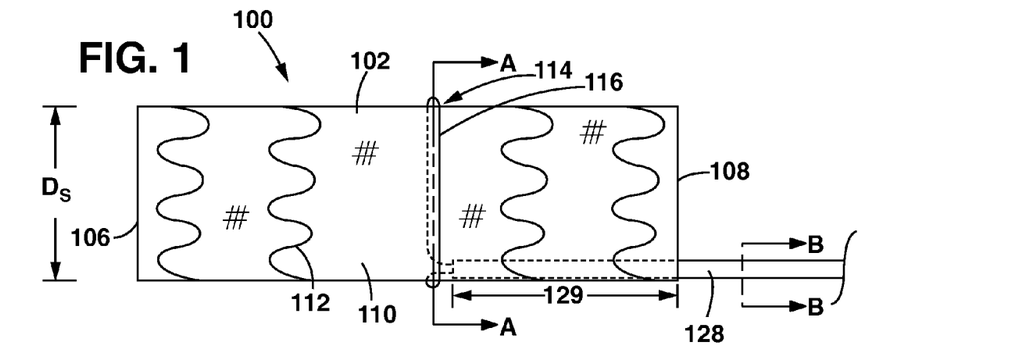
FIG. 1 is a side view of an AV shunt assembly including a flow control mechanism according to an embodiment hereof, wherein the AV shunt assembly is shown deployed in a fully open configuration.

Embodiments hereof are directed to apparatuses and methods for creating an artificial arteriovenous fistula or connection between an artery and an adjacent vein with an arteriovenous (AV) shunt assembly that includes a shunt having a flow control mechanism for selectively controlling flow through the shunt in vivo. Referring to FIG. 1, an arteriovenous (AV) shunt assembly 100 includes a tubular shunt or conduit 102 and a flow control or pull-wire mechanism 114 for controlling or otherwise adjusting the rate of blood flow through shunt 102. Tubular shunt 102 defines a fluid passageway 104 (shown in FIG. 1A) that extends between a first or inflow end 106 and a second or outflow end 108. Pull-wire mechanism 114 may be selectively tightened or loosened around tubular shunt 102 in order to regulate the rate of flow permitted through fluid passageway 104 of shunt 102 as will be described in more detail herein. Pull-wire mechanism 114 is configured such that a physician may adjust or control the flow through the shunt assembly in situ. Adjustments of the flow may be necessary to see positive effects/improvement in the patient's condition, i.e., to maximize blood oxygenation in the treatment of COPD. Further, having the ability to adjust the rate of flow post implantation of the AV shunt gives the physician the ability to make performance adjustments over time without having to remove the shunt.

Tubular shunt 102 is a stent graft comprising graft material 110 having a plurality of radially compressible stents 112 attached thereto. FIG. 1 illustrates four stents 112 attached to graft material 110; however, a greater or lesser number of stents may be utilized. Stents 112 are radially compressible and may be of known stent constructions such as laser-cut or etched tubes or wavelike or sinusoidal patterned wire rings that are biased in a radially outward direction to an expanded diameter. Stents 112 are formed from a self-expanding elastic or superelastic material, such as a nickel-titanium alloy (nitinol), to return to an expanded deployed configuration from a compressed or collapsed delivery configuration as described for example, in U.S. Pat. No. 5,713,917 and U.S. Pat. No. 5,824,041, which are incorporated by reference herein in their entirety. Stents 112 may be attached or mechanically coupled to graft material 110 by various means, such as, for example, by stitching or suturing onto either the inside or outside of graft material 110. Although shown as coupled to an exterior surface of graft material 110, stents 112 may alternatively be coupled to an interior surface of graft material 110. Further, although stents 112 are shown as a plurality of individual wire rings, it will be understood by one of ordinary skill in the art that the stents 112 may have various other configurations that are suitable for forming a fluid connection between an artery and an adjacent vein. For example, the tubular shunt may include a continuous tubular stent framework, e.g., a mesh or lattice scaffolding, attached to graft material 110.

Graft material 110 creates a conduit or fluid passageway when attached to stents 112. Graft material 110 may be expanded polytetrafluoroethylene (ePTFE) or a low-porosity knit or woven polyester fabric, either of which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 110 could also be a natural material such as pericardium or another membranous tissue such as intestinal submucosa.

Pull-wire mechanism 114 includes a continuous wire or filament 116 and an elongated shaft 128 for housing wire 116. Shaft 128 is an extruded tubular component defining a first lumen 130 (shown in FIG. 1B) and a second lumen 132 (also shown in FIG. 1B). Lumens 130, 132 are sized to slidingly receive wire 116 there through. Alternatively, shaft 128 may have only a single lumen through which both ends of wire 116 extend side-by-side. Shaft 128 may be formed of any suitable flexible polymeric material such as, but not limited to polyethylene terephalate (PET), nylon, polyethylene, polyethylene block amide copolymer, or combinations of any of these, either blended or co-extruded. An integral distal end segment 129 of shaft 128 is coupled to an inside surface of tubular shunt 102 via adhesive or other mechanical method, while the remaining length of shaft 128 proximally extends away from tubular shunt 102 to a subcutaneous port that will be discussed in more detail herein. As shown in FIG. 1, distal end segment 129 may extend approximately to a longitudinal midpoint of tubular shunt 102 where a distal portion of wire 116 exits shaft 128 to encircle tubular shunt 102. Alternatively, end segment 129 may extend to any longitudinal location or position along the tubular shunt where it is desirable for wire 116 to encircle tubular shunt 102. An outer surface of tubular shunt 102 may include a track similar to track 1372 (FIGS. 13-14) formed thereon to ensure that wire 116 follows the desired pathway around the tubular shunt. Shaft 128 may have any suitable working length, for example, 150 mm, in order to extend to a target location where AV shunt assembly 100 is to be implanted. An outer diameter of shaft 128 may range from but is not restricted to 0.030-0.040 inch.

Figure 3:
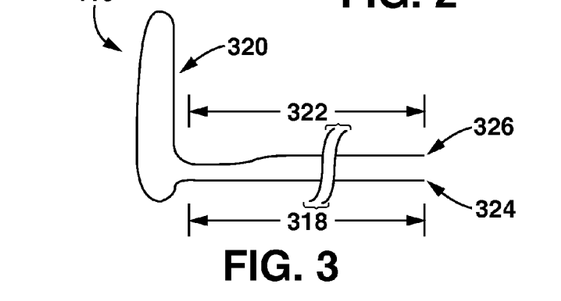
FIG. 3 is a side view illustration of a pull wire of the flow control mechanism of FIG. 1 removed from the AV shunt assembly.

FIG. 3 illustrates wire 116 removed from the AV shunt assembly of FIG. 1. Wire 116 is a continuous or unitary filament that when wrapped around a circumference of shunt 102 may be described as having a first elongated portion or leg 318, a second elongated portion or leg 322, and a distal portion 320 which is looped around tubular shunt 102. Looped distal portion 320 of wire 116 may be selectively tightened or loosened in order to vary the size of fluid passageway 104 and thereby regulate the rate of blood flow through AV shunt assembly 100. When wrapped around the shunt circumference, wire 116 may also be described as having a first proximal end 324 and a second proximal end 326 with each end 324, 326 of wire 116 proximally extending out of shaft 128 to be operatively coupled within a subcutaneous port to permit manipulation by a clinician as will be discussed in more detail herein. As shown in FIG. 1B, first elongated leg 318 extends through first lumen 130 of shaft 128 and second elongated leg 322 extends through second lumen 132 of shaft 128. Distal portion 320 is not contained within shaft 128 but rather forms at least one loop that surrounds an outer perimeter of tubular shunt 102 at an axial location between shunt ends 106, 108. The path taken by wire 116 in shunt assembly 100 can be described as follows. Wire 116 extends through shaft lumen 130, exits from a distal end of shaft 128, passes through shunt graft material 110, loops around the outside of tubular shunt 102, passes back through graft material 110 of tubular shunt 102, reenters the distal end of shaft 128, and extends through shaft lumen 132. The cross-section of wire 116 may be circular, as shown in FIG. 1B, or may have one or more alternative cross-sections along its length, as known to those of ordinary skill in the art, including but not limited to tubular, rectangular, or elliptical. Wire 116 is formed from a material of sufficient strength to close flow control mechanism 114 when tension is applied to one or both ends 324, 326. Suitable materials for wire 116 include but are not limited to medical grade stainless steel, nickel-cobalt-chromium-molybdenum superalloy, nitinol or non-absorbable surgical suture material such as braided or monofilament polyamide, polypropylene, polyethylene, polyester, or polybutester. Wire 116 may range, but without limitation, from 0.010-0.20 inch in diameter.

Figure 2:
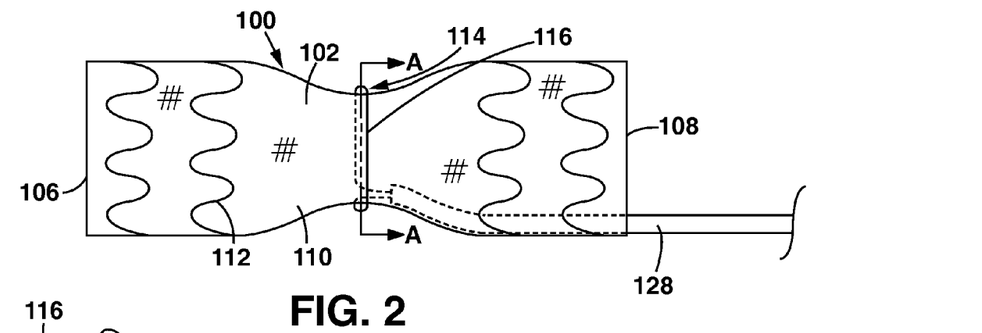
FIG. 2 is a side view of the AV shunt assembly of FIG. 1, wherein the AV shunt assembly is shown deployed in a partially closed configuration.
Figure 4:
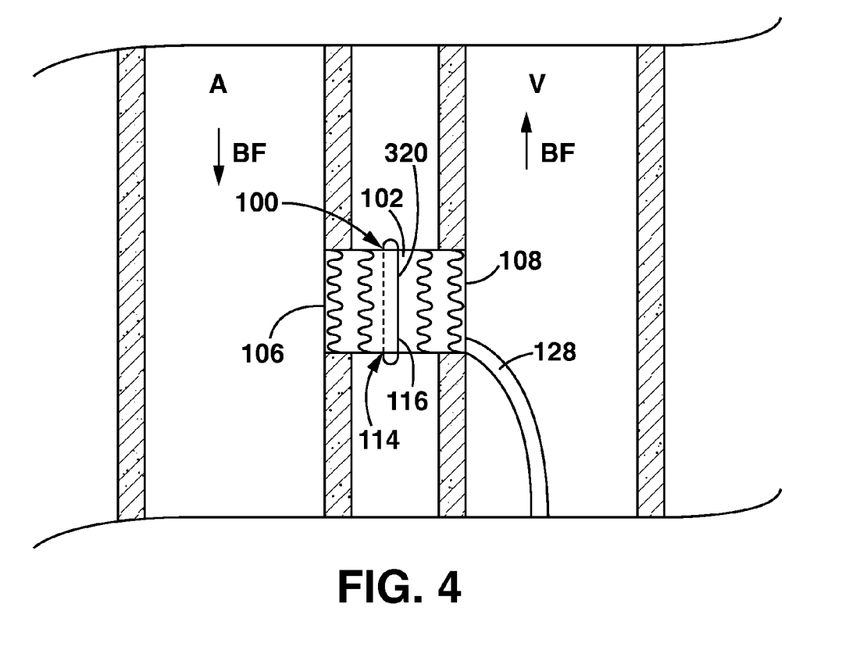
FIGS. 4 and 5 are side view illustrations showing the AV shunt assembly deployed in situ in fully open and partially closed configurations, respectively.
Figure 5:
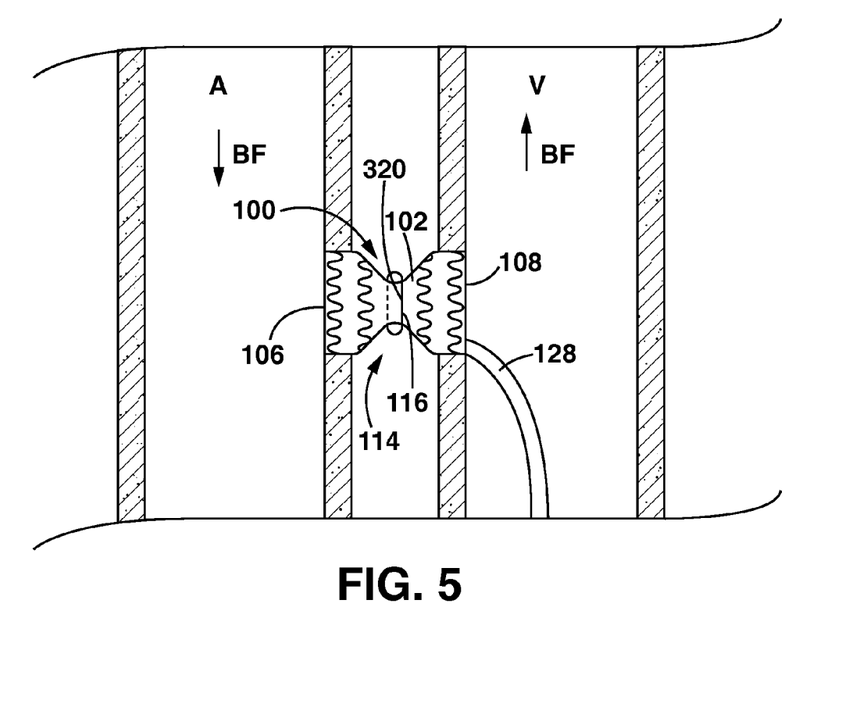

FIGS. 1 and 2 are side views illustrating AV shunt assembly 100 deployed in a fully open configuration and a partially closed configuration, respectively, while FIGS. 4 and 5 are corresponding side view illustrations of AV shunt assembly 100 deployed in situ with tubular shunt 102 extending between an artery A and an adjacent vein V. In one embodiment, artery A and vein V are the femoral artery and femoral vein of a patient's leg. However, embodiments hereof may be deployed in any two adjacent body lumens or cavities in which it is desirable to form an adjustable fluid flow connection. Blood flow BF is indicated in the figures with directional arrows. As known by one of ordinary skill in the art, when circulating through a body with no AV shunts in place, oxygenated blood flows away from the heart to the tissue through arteries and capillaries and then following the release of oxygen in the tissues, the blood returns in veins to the heart. Arterial blood has a higher blood pressure than blood in veins. When an AV shunt is in place, the blood pressure difference causes some arterial blood to bypass the capillaries and tissues and instead be diverted into the vein via the shunt to return to the heart. Accordingly, AV shunt assembly 100 in either an open or partially closed configuration diverts some of the blood flowing through artery A into vein V.

Figure 1A:
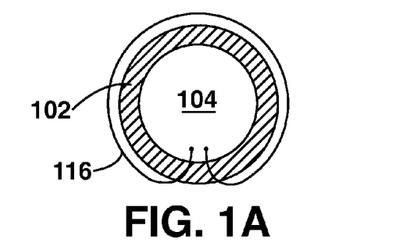
FIG. 1A is a cross-sectional view taken along line A-A of FIG. 1.
Figure 1B:
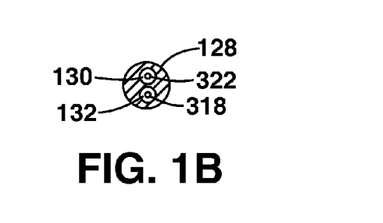
FIG. 1B is a cross-sectional view taken along line B-B of FIG. 1.
Figure 2A:
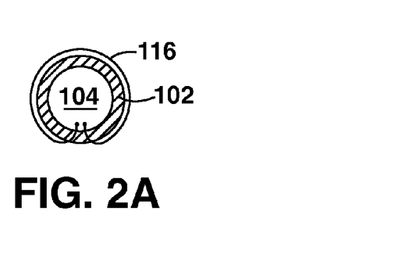
FIG. 2A is a cross-sectional view taken along line A-A of FIG. 2.

When AV shunt assembly 100 is in the fully open configuration of FIGS. 1, 1A and 4, looped distal portion 320 of wire 116 is not constricting tubular shunt 102 such that fluid passageway 104 is in its fully open or expanded configuration, to allow a maximum rate of blood flow through AV shunt assembly 100. When sufficient tension is applied to wire 116 as will be described in more detail herein, looped distal portion 320 tightens around or exerts a radially inward force onto tubular shunt 102 to narrow or constrict fluid passageway 104 into the partially closed or restricted flow configuration shown in FIGS. 2, 2A and 5. Although distal portion 320 is shown slightly spaced apart from the outer surface of tubular shunt 102, it will be understood by those of ordinary skill in the art that the gap is for illustrative purposes only and in operation, distal portion 320 more typically abuts against the outer surface of tubular shunt 102, especially when wire 116 is constricting the diameter of shunt 102. When fluid passageway 104 is narrowed, the rate of blood flow permitted through AV shunt assembly 100 is reduced. To maintain AV shunt assembly 100 in the partially closed configuration, tension is maintained in wire 116. If it is desired to completely close fluid passageway 104, the distal portion 320 of wire 116 is tightened around tubular shunt 102, with increased tension if necessary, until blood flow is blocked through fluid passageway 104 of the shunt. Alternatively, if it is desired to re-open fluid passageway 104 to its fully open configuration, the tension in wire 116 is released and tubular shunt 102 is permitted to resume its fully expanded configuration via self-expanding stents 110 with some assistance from the blood pressure within the shunt. In addition, blood flow will fully open fluid passageway 104 of tubular shunt 102 when distal portion 320 of wire 116 is not exerting a radially inward force onto the shunt.

FIG. 2 and FIG. 5 illustrate a partially closed or restrictive flow configuration of fluid passageway 104 by way of example and not limitation. It will be understood by one of ordinary skill iii the art that flow control mechanism 114 may be utilized to adjust a diameter of fluid passageway 104 to any of numerous restrictive flow configurations between fully open and fully closed states. More particularly, the various positions of shunt fluid passageway 104 between a fully open configuration and a fully closed configuration may be achieved as distal portion 320 of wire 116 of flow control mechanism 114 is tightened around tubular shunt 102. The rate of blood flow through shunt 102 may be regulated by controlling the length of distal portion 320 extending from shaft 128. If distal portion 320 is only shortened a small amount by pulling one or both of wire legs 318, 322 into shaft 128, then fluid passageway 104 is minimally constricted and a relatively large volume of oxygenated blood is permitted to flow through shunt 102. Conversely, if a greater length of one or both of wire legs 318, 322 is drawn into shaft 128 to shorten distal portion 320, then fluid passageway 104 is more constricted and a relatively smaller volume of oxygenated blood is permitted to flow through shunt 102. Accordingly, the physician may incrementally adjust the length of wire 116 extending from shaft 128 to form distal portion 320 in order to increase or decrease blood flow through AV shunt assembly 100 as necessary in order to optimize performance of AV shunt assembly 100. For example, if additional improvement of blood oxygenation is necessary or desirable, a length of wire 116 is incrementally released from shaft 128 to lengthen distal portion 320 in order to increase the rate of blood flow through the shunt. After adjustment, the patient's blood oxygenation may be measured again to determine changes therein due to the flow control mechanism position adjustment and a determination may then be made whether additional adjustment(s) are necessary or desirable. It will be understood by one of skill in the art that tightening looped distal portion 320 may require increasing the tension applied to one or both of wire legs 318, 322 in proportion to the circumferential force required to constrict shunt assembly 100, especially if one or more of stents 112 are being radially compressed.

Tubular shunt 102 may include a plurality of self-transforming anchors (not shown) that radially extend from both inflow and outflow ends 106, 108 of tubular shunt 102 when deployed in order to secure the shunt in place between artery A and vein V as described in U.S. patent application Ser. No. 13/365,994, filed Feb. 3, 2012. Anchors positioned at inflow end 106 of tubular shunt 102 radially extend against a vessel wall of artery A and anchors positioned at outflow end 108 of tubular shunt 102 radially extend against a vessel wall of vein V.

Figure 6:
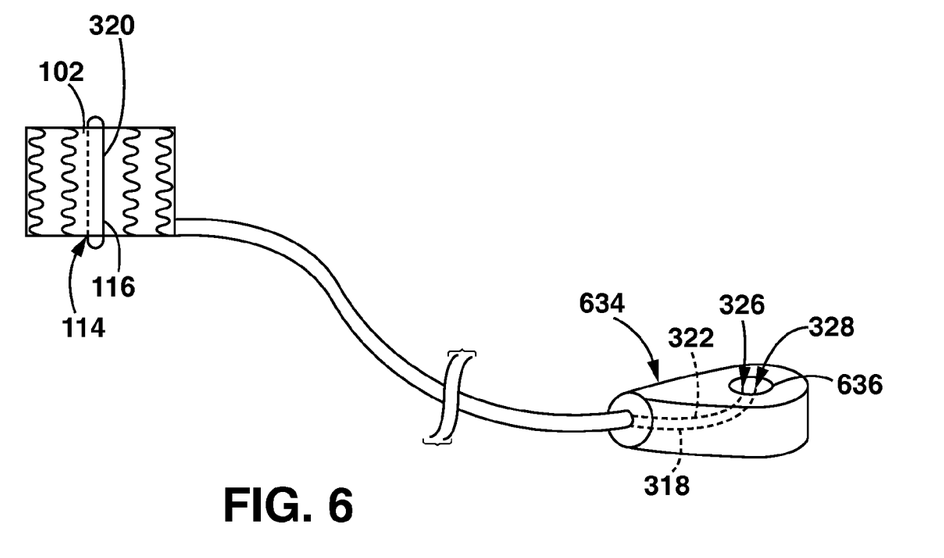
FIG. 6 is a side view illustration of the AV shunt assembly of FIG. 1 including a proximal subcutaneous access port.

As illustrated in FIG. 6, shaft 128 extends from tubular shunt 102 to a control port 634, which is implanted subcutaneously, in order to be easily accessed by a physician. Shaft 128 is sealingly coupled to control port 634, and legs 318, 322 of wire 116 of flow control mechanism 114 extend through an opening 636 formed in control port 634 such that proximal ends 324, 326 of wire 116 are accessible to the physician. More particularly, with control port 634 implanted subcutaneously, proximal ends 324, 326 of wire 116 are located just under a patient's skin and may be accessed in order to apply tension or pull on one or both of proximal ends 324, 326 of wire 116. In one embodiment, a small incision may be formed through the patient's skin in order to manually access wire 116. In another embodiment, saline may be injected into opening 636 of control port 634 via a needle inserted through the skin and a septum that seals opening 636. The injected saline applies pressure to a piston or diaphragm that pulls on or applies tension to proximal ends 324, 326 of wire 116.

For percutaneous delivery, wire 116 is positioned around tubular shunt 102 and within first and second lumens 130, 132 of shaft 128 as described above and AV shunt system 100 is radially compressed to a low-profile delivery configuration and is mounted onto a percutaneous delivery system (not shown). The delivery system may include a catheter and an outer retractable sheath. Tubular shunt 102 having distal portion 320 of wire 116 disposed thereover is mounted over an inner shaft of the catheter at the distal end thereof and the sheath surrounds and constrains AV shunt assembly 100 in a delivery configuration. Shaft 128, having elongated leg portions 318, 322 of wire 116 therein, extends within the delivery system between the inner shaft and the outer sheath. In one embodiment, the catheter may include a retainer which temporarily secures a proximal end of tubular shunt 102 onto the inner shaft. For example, the retainer may include an end stent capture configuration as described in U.S. Patent Pub. 2009/0276027 to Glynn, which is hereby incorporated by reference herein in its entirety.

As will be understood by one of ordinary skill in the art, the delivery system is introduced through a percutaneous tissue tract from the skin into vein V and navigated through the vasculature until AV shunt assembly 100 is positioned through a fistular tissue tract that extends through the wall of vein V, through any intervening tissue and/or hollow space between vein V and artery A, and through the wall of artery A to thereby extend between the lumens of vein V and artery A. The delivery system may be modified to create the fistular tissue tract, or the fistular tissue tract may have been previously formed by a separate tissue penetrating catheter device (not shown) as would be known to one of skill in the art. The PIONEER tissue penetrating catheter, commercially available from Medtronic CardioVascular, Inc., Santa Rosa, Calif., is suitable for use in embodiments described herein. Optionally, in some applications of this method, one or more tract modifying devices such as balloon catheters and/or atherectomy catheters may be used to enlarge, dilate, debulk, and/or bore the fistular tissue tract after which they are removed. Examples of tract modifying devices and procedures of this sort are provided in U.S. Pat. No. 5,830,222 to Makower and U.S. Pat. No. 6,561,998 to Roth et al., the disclosures of which are hereby incorporated by reference herein in their entireties.

To deploy AV shunt assembly 100, the outer sheath is proximally retracted in order to permit tubular shunt 102 to expand, thereby resulting in the uncoupling of the shunt from the catheter. The delivery system can then be retracted from the patient, leaving the expanded tubular shunt extending between artery A and vein V. It is expected that AV shunt assembly 100 is percutaneously inserted into a vein such that the fistular tissue tract is approached from the venous end. After the shunt assembly 100 is deployed from the delivery system, shaft 128 extends through vein V and into the percutaneous tissue tract. Expanded tubular shunt 102 creates a blood flow passageway or connection between artery A and vein V, as shown in FIGS. 4 and 5 above. In an embodiment, shaft 128 and/or wire 116 may be cut to length and attached to control port 634 which is then implanted subcutaneously in the percutaneous tissue tract, similar to the arrangements illustrated in FIGS. 12 and 14. After AV shunt assembly 100 is implanted, the flow there through may be adjusted in situ using flow control mechanism 114 by varying the length of distal portion 320 extending from shaft 128 as described above. Alternatively, the AV shunt assembly 100 is percutaneously inserted into the artery such that the fistular tissue tract is approached from the arterial end.

Figure 7:
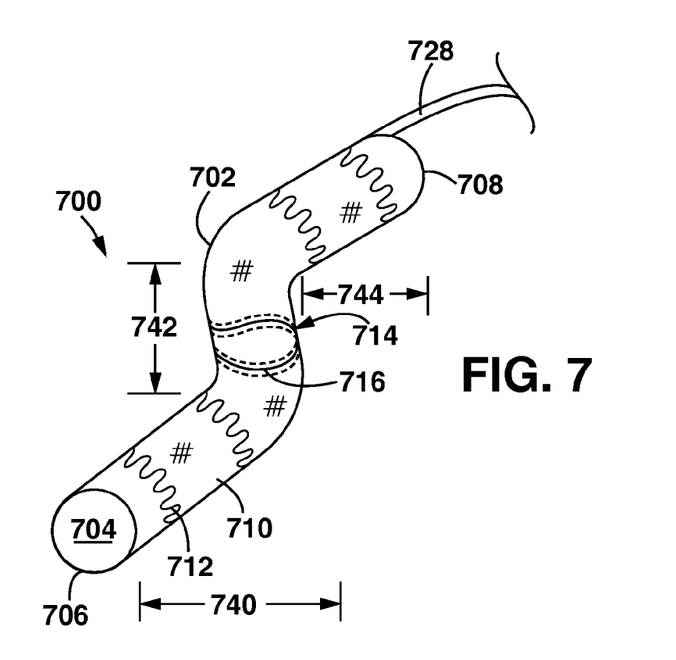
FIG. 7 is a side view of an AV shunt assembly according to another embodiment hereof, wherein a tubular shunt includes a longitudinal arterial portion and a longitudinal vein portion.

FIG. 7 is a side view of an AV shunt assembly 700 according to another embodiment hereof, wherein portions of the shunt are configured for placement within the artery and vein. More particularly, AV shunt assembly 700 includes a tubular shunt or conduit 702 defining a fluid, passageway 704 and a pull-wire or flow control mechanism 714. Similar to pull-wire mechanism 114 described above, a wire 716 of pull-wire mechanism 114 may be tightened or loosened around tubular shunt 102 in order to regulate the rate of blood flow permitted through tubular shunt 702. Tubular shunt 702 includes graft material 710 having a plurality of radially compressible stents 712 attached thereto. However, unlike tubular shunt 102, tubular shunt 702 includes a first end or arterial segment 740 configured for placement in an artery, a second end or vein segment 744 configured for placement in a vein, and an intermediate segment 742 between first and second end segments 740, 744 for extending through a tissue tract between the artery and the vein as described in as described in U.S. patent application Ser. No. 13/404,477, filed Feb. 24, 2012, herein incorporated by reference in its entirety. Tubular shunt 702 has an expanded diameter which is less than the luminal diameters of the artery and vein, and when deployed in situ, first and second end segments 740, 744 are pushed toward each other to lie against adjacent walls of adjacent vessels and extend parallel to blood flow within the artery and vein, respectively. Orienting end segments 740, 744 to longitudinally extend within the artery and vein, respectively, beneficially directs the fluid flow into an inflow end 706 thus serves to improve the hemodynamics of blood flow through the shunt. In addition, since tubular shunt 702 has a smaller expanded diameter than the target vessels, the shunt diverts or bypasses only some of the blood flow within the artery. Such partial diversion or bypass ensures that sufficient oxygenated blood is supplied to tissue downstream of the artery as well as back to the heart via the shunt.

Figure 8:
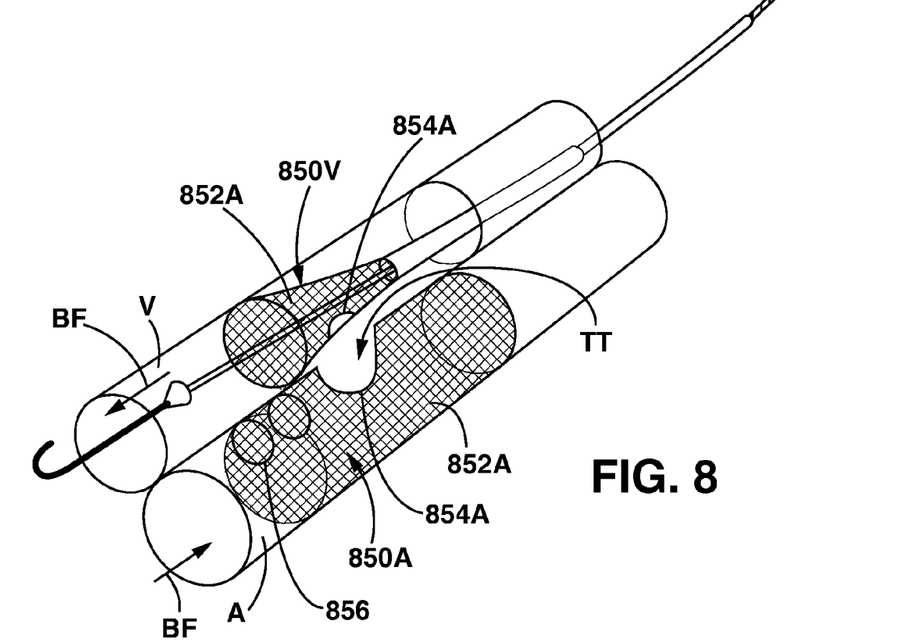
FIGS. 8-12 illustrate a method of forming a connection between an artery A and an adjacent vein V and controlling blood flow through the connection, wherein the method utilizes the AV shunt assembly of FIG. 7.
Figure 9:
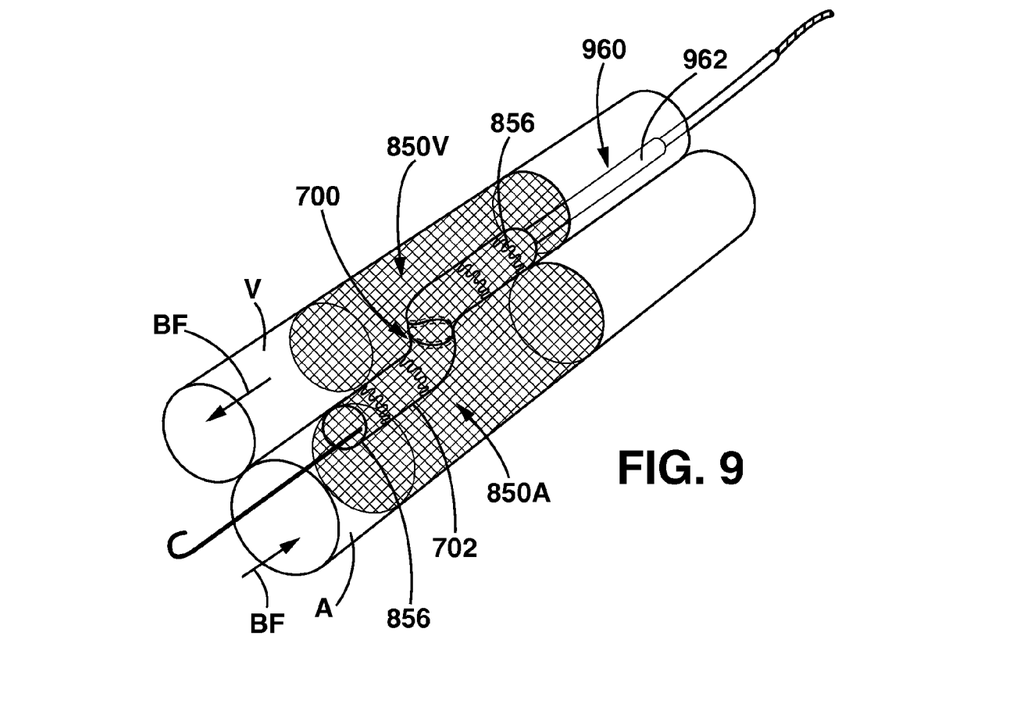
Figures 10, 11:
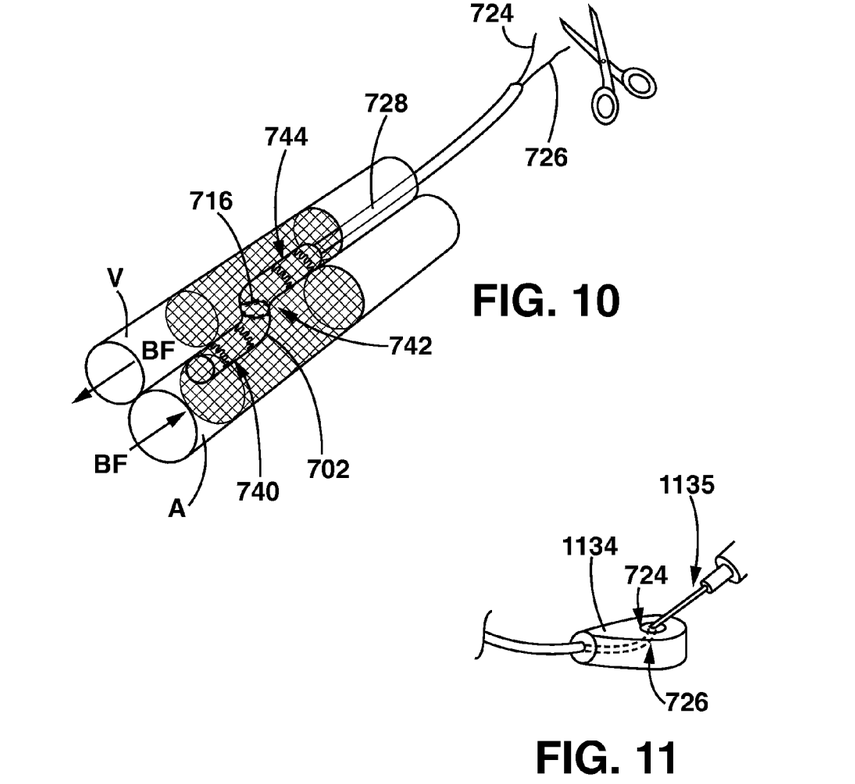

FIGS. 8-12 illustrate a method of forming a connection between an artery A and an adjacent vein V with AV shunt assembly 700. Initially, as shown in FIG. 8, a self-expanding tubular anchor 850 is deployed within each of artery A and vein V. Anchor 850 is described in U.S. patent application Ser. No. 13/404,477, filed Feb. 24, 2012, previously incorporated by reference herein. Each anchor 850 includes a self-expanding tubular body 852 sized such that anchor 850 expands into apposition fully around the interior wall of a target vessel. Each anchor 850 also includes a side port or opening 854 formed within tubular body 852 that is sized to permit passage of tubular shunt 702, and an interior ring or scaffold 856 for receiving and securing tubular shunt 702 against the inside surface of the body 852. As shown in FIGS. 8-10, when utilized to anchor and position an AV shunt, one anchor 850 is deployed in an artery A and one anchor 850 is deployed in a vein V. For sake of convenience, the anchor deployed in artery A will herein be referred to as anchor 850A and the anchor deployed in vein V will herein be referred to as anchor 850V although anchors 850A, 850V are identical structures. Anchor 850A is delivered and deployed within artery A such that tubular body 852A expands into apposition fully around the interior of artery A and opening 854A is aligned with a fistular tissue tract TT, which may be formed by a delivery catheter (not shown) during deployment of anchor 850A or may have been previously formed by a separate tissue penetrating catheter device (not shown) as would be known to one of skill in the art. Similarly, anchor 850V is delivered and deployed within vein V such that tubular body 852V expands into apposition fully around the interior of vein V and opening 854V is aligned with fistular tissue tract TT.

After anchors 850 are delivered and deployed, an AV shunt assembly 700 is delivered and deployed through the fistular tissue tract, with anchors 850A, 850V radially offsetting tubular shunt 702 within each of artery A and vein V. Utilizing a delivery device 960, AV shunt assembly 700 is threaded through rings 856 of anchor 850A, through side opening 854A of anchor 850A, through fistular tissue tract TT, through side opening 854V of anchor 850V, and through rings 856 of anchor 850V. As shown in FIG. 9, an outer sheath 962 of delivery system 960 is proximally retracted to allow stents 712 (obscured from view in FIG. 9) to self-expand into apposition with rings 856 of anchors 850A, 850V.

Figure 12:
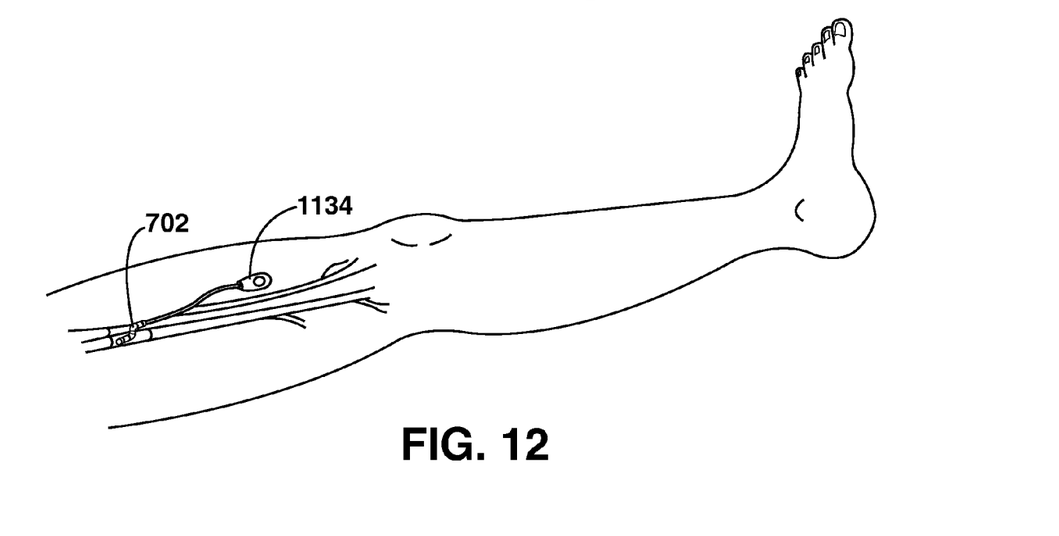

Delivery system 960 can then be retracted from the patient, leaving tubular shunt 702 deployed such that arterial segment 740 extends within artery A and is radially offset therein, vein segment 744 extends within vein V and is radially offset therein, and intermediate segment 742 extends between artery A and vein V. Intermediate segment 742 includes wire 716 of the flow control mechanism wrapped or looped around the outer perimeter of tubular shunt 702 for selectively controlling the rate of blood flow through the fluid passageway of the shunt. Shaft 728 extends from shunt 702 through vein V and a percutaneous tissue tract, and shaft 728 and/or ends 724, 726 of wire 716 may be cut to length as shown in FIG. 10. After the length of wire 716 is sized as desired, ends 724, 726 of wire 716 are coupled to port 1134 as shown in FIG. 11. Port 1134 is implanted subcutaneously in the percutaneous tissue tract at a location spaced apart or remote from implanted tubular shunt 702, as shown in FIG. 12 which shows tubular shunt 702 implanted between a femoral artery and a femoral vein of a patient's leg. After implantation, the flow through tubular shunt 702 may be adjusted in situ by flow control mechanism 714, i.e. by manipulating one or both ends of wire 716 as described above with respect to flow control mechanism 114. For example, saline may be injected into port 1134 via a needle 1135 (shown in FIG. 11) in order to apply tension to ends 724, 726 of wire 716. Alternatively, a small incision may be formed through the patient's skin in order to access ends 724, 726 of wire 716 and a physician may manually pull on at least one of the ends of the wire.

In another embodiment (not shown), rather than using tubular anchors 850, tubular shunt 702 may be radially offset within the artery and vein via oversized eccentric anchor stents positioned at each end of the shunt as also described in U.S. patent application Ser. No. 13/404,477, filed Feb. 24, 2012, previously incorporated by reference.

Figure 13:
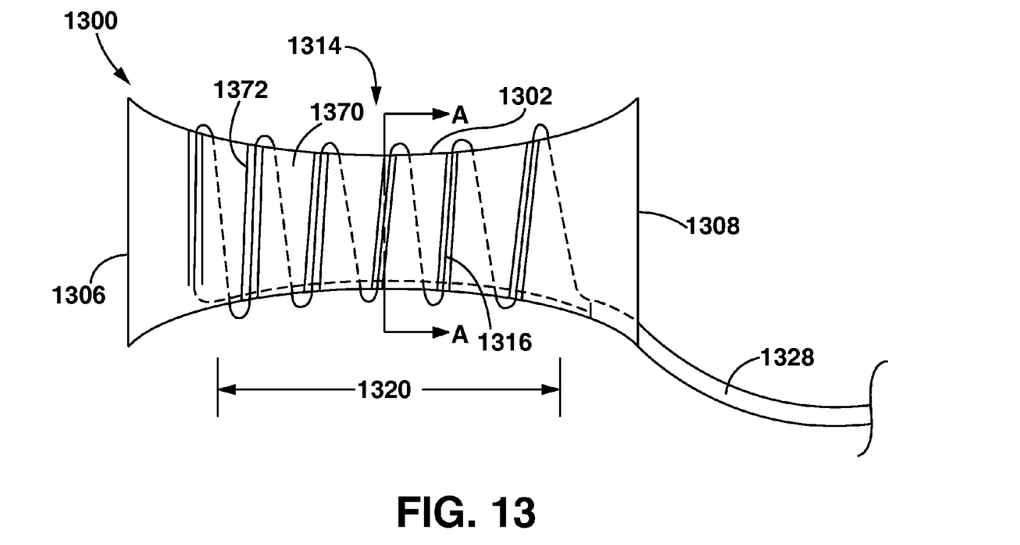
FIG. 13 is a side view of an AV shunt assembly according to another embodiment hereof, wherein a flow control mechanism includes a distal portion disposed around a tubular shunt in a series of spaced apart loops.
Figure 13A:
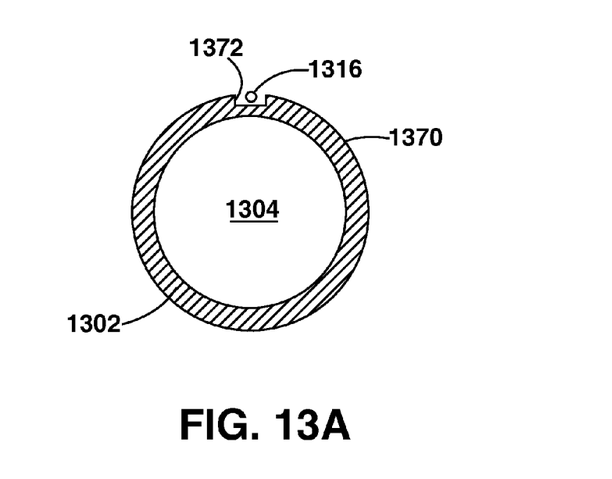
FIG. 13A is a cross-sectional view taken along line A-A of FIG. 13.
Figure 14:
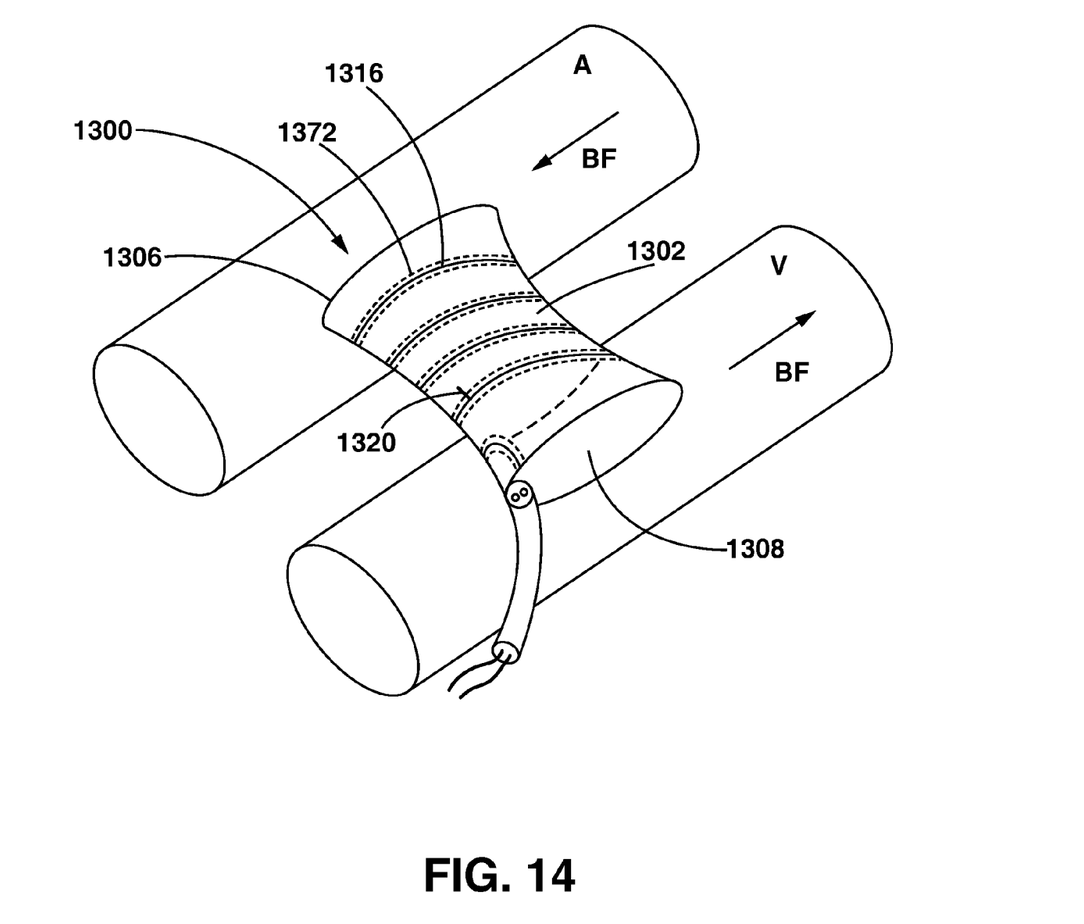
FIG. 14 is a side view illustration showing the AV shunt assembly of FIG. 13 deployed in situ in a fully open configuration.

FIGS. 13, 13A, and 14 illustrate another embodiment of an arteriovenous (AV) shunt assembly 1300 that includes a tubular shunt or conduit 1302 and a pull-wire mechanism 1314. Similar to AV shunt assembly 100, tubular shunt 1302 defines a fluid passageway 1304 (shown in FIG. 13A) therethrough that extends between a flared inflow end 1306 and a flared outflow end 1308. Flared inflow and outflow ends 1306, 1308 have a greater diameter than a middle or center portion of tubular shunt 1302 in order to anchor the shunt in situ between the artery and the vein. Pull-wire or flow control mechanism 1314 includes a continuous wire or cable 1316 and an elongated shaft 1328 for housing wire 1316, and pull-wire mechanism 1314 may be tightened or loosened around tubular shunt 1302 in order to regulate the rate of blood flow permitted through fluid passageway 1304 of shunt 1302. However, in this embodiment, wire 1316 includes a distal portion 1320 disposed around tubular shunt 1302 in a series of spaced apart loops rather than a single loop as described above with respect to AV shunt assembly 100. Distal portion 1320 of wire 1316 spirals or wraps around tubular shunt 1302 in a corkscrew manner. Operation of flow control mechanism 1314 regulates the rate of flow through the shunt in a similar manner as described with respect to flow control mechanism 114. When AV shunt assembly 1300 is in the fully open configuration illustrated in FIGS. 13 and 14, distal portion 1320 of wire 1316 is not constricting or exerting a tightening force onto tubular shunt 1302 and thus a maximum rate of blood flow is permitted through tubular shunt 1302. When tension is applied to one of the proximal ends of wire 1316, coiled distal portion 1320 tightens around or exerts a radially inward force onto tubular shunt 1302 to uniformly narrow or constrict fluid passageway 1304. When fluid passageway 1304 is narrowed, the rate of blood flow permitted through AV shunt assembly 1300 is reduced.

In this embodiment, tubular shunt 1302 is constructed from a stent-graft as described above. An outer surface 1370 of tubular shunt 1302 includes a track 1372 formed thereon to ensure that wire 1316 follows the desired coil or spiral pathway around the tubular shunt. In the embodiment illustrated in FIG. 13B, track 1372 includes a groove or recess formed within the material of tubular shunt 1302. In another embodiment (not shown), track 1372 may include a pocket or internal channel formed within the material of tubular shunt 1302. In yet another embodiment (not shown), track 1372 may include a series of tabs or belt loops coupled to outer surface of 1370 of tubular shunt 1302 and wire 1316 may be slidingly threaded there through. In another embodiment, the pull wire may be woven in and out of the shunt material to keep it in position. Such an embodiment would function similar to a purse-string suture technique for closure/tightening. Although track 1372 is shown with respect to wire 1316 having a distal portion 1320, it will be understood by those of ordinary skill in the art that a track may be utilized with any embodiment described herein, including those embodiments in which the distal portion of the wire forms a single loop around the tubular shunt.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An arteriovenous shunt assembly comprising:
   a tubular shunt having a fluid passageway between open first end second ends thereof;
   a flow control mechanism that includes a pull wire having a distal portion disposed circumferentially around the tubular shunt in at least one loop; and
   a subcutaneous control port containing ends of the pull wire and an opening for percutaneous access to the ends of the pull wires, wherein pulling on at least one of the ends of the pull wire causes the pull wire to selectively tighten around the tubular shunt and radially constrict the tubular shunt, thereby reducing the rate of blood flow permitted through the fluid passageway of the tubular shunt.

2. The arteriovenous shunt assembly of claim 1, wherein the tubular shunt includes graft material having a plurality of self-expanding stents attached thereto.

3. The arteriovenous shunt assembly of claim 1, wherein the at least one loop of the distal portion of the flow control mechanism is disposed around an outer surface of the tubular shunt.

4. The arteriovenous shunt assembly of claim 1, wherein the at least one loop of the distal portion is a series of spaced apart loops disposed around the tubular shunt.

5. The arteriovenous shunt assembly of claim 1, wherein the at least one loop of the distal portion of the flow control mechanism is positioned approximately at the longitudinal midpoint of the tubular shunt.

6. The arteriovenous shunt assembly of claim 1, wherein the flow control mechanism also includes an elongated shaft defining a first lumen for slidingly receiving a first elongated leg of the wire and a second lumen for slidingly receiving a second elongated leg of the wire, the elongated shaft having a distal end segment coupled to an inside surface of the tubular shunt and a proximal end coupled to the subcutaneous control port.

7. The arteriovenous shunt assembly of claim 1, wherein the first and second ends of the tubular shunt have a larger outer diameter than a middle portion of the tubular shunt.

8. A method for forming a connection between a first body vessel and a second body vessel for controlling blood flow through the connection, the method comprising the steps of:
   intravascularly delivering a shunt assembly in its collapsed configuration to a tissue tract formed between the first vessel and the second vessel, the shunt assembly including a tubular shunt that defines a fluid passageway between a first end and a second end thereof and a flow control mechanism coupled to the shunt, wherein the flow control mechanism includes a continuous pull wire having a distal portion disposed around the tubular shunt in at least one loop;
   positioning the tubular shunt through the tissue tract;
   deploying the tubular shunt to an expanded configuration;
   pulling on an end of the pull wire to tighten the at least one loop of the distal portion to radially constrict the tubular shunt and thereby reduce the rate of blood flow permitted through the fluid passageway of the tubular shunt;
   wherein the step of pulling on an end of the pull wire includes forming a small incision through the patient's skin in order to access ends of the wire; and pulling on at least one of the ends of the wire.

9. The method of claim 8, wherein first vessel is an artery and the second vessel is a vein adjacent to the artery.

10. The method of claim 9, wherein the artery is a femoral artery in a leg and the vein is a femoral vein in the leg, and the step of longitudinally shifting the flow control mechanism provides treatment for COPD.

11. The method of claim 8, wherein the step of deploying the tubular shunt includes retracting a sheath of a delivery system.

12. The method of claim 8, wherein the at least one loop of the distal portion is disposed within a track formed within an outer surface of the tubular shunt.

13. The method of claim 8, wherein the at least one loop of the distal portion is a series of spaced apart loops disposed around the tubular shunt.

14. The method of claim 8, wherein the at least one loop of the distal portion is positioned approximately at the longitudinal midpoint of the tubular shunt.

15. The method of claim 8, wherein the flow control mechanism also includes an elongated shaft defining a first lumen for slidingly receiving a first elongated leg of the wire and a second lumen for slidingly receiving a second elongated leg of the wire, the elongated shaft having a distal end segment coupled to an inside surface of the tubular shunt.

* * * * *